United States Patent [19]
Curtiss

[11] 3,934,753
[45] Jan. 27, 1976

[54] DISC DISPENSER WITH REMOVABLE MAGAZINES

[75] Inventor: Alan C. Curtiss, Old Lyme, Conn.

[73] Assignee: Pfizer Inc., New York, N.Y.

[22] Filed: Jan. 29, 1974

[21] Appl. No.: 437,700

[52] U.S. Cl. ..................... 221/93; 133/4 R; 221/198
[51] Int. Cl.² .......................................... B65H 3/44
[58] Field of Search ...... 221/93, 198, 279; 133/4 R, 133/5 R, 5 A

[56] References Cited
UNITED STATES PATENTS

| | | | |
|---|---|---|---|
| 2,132,229 | 10/1938 | Breitenstein | 133/4 R |
| 2,445,026 | 7/1948 | Frank | 221/279 X |
| 2,491,573 | 12/1949 | McPherson | 133/5 R |
| 2,532,976 | 12/1950 | Weirich | 133/4 R |
| 2,696,324 | 12/1954 | Jones | 221/198 X |
| 2,865,156 | 12/1958 | Wolfson | 221/93 X |
| 3,300,087 | 1/1967 | Kuypers | 221/93 |
| 3,394,846 | 7/1968 | Carski | 221/93 |

FOREIGN PATENTS OR APPLICATIONS

| | | | |
|---|---|---|---|
| 687,149 | 5/1964 | Canada | 221/93 |

Primary Examiner—Drayton E. Hoffman
Assistant Examiner—Francis J. Bartuska
Attorney, Agent, or Firm—Connolly & Hutz

[57] ABSTRACT

A number of discs are simultaneously dispensed into a culture dish from a dispenser having an array of self-contained dispensers locked in apertured sockets on a base frame. The individual dispensers are simultaneously operated by an actuating plate which engages actuating pins on each of them. The height of the dispenser above the culture dish is adjustable by cam and follower engagement of the base plate within a height-adjusting ring. Indicia and yieldable detents are provided for indexing the height of the base plate. The individual dispensers each include a chute-incorporating body, cover, slide plate, spring and tubular cartridge. The open tops of the chutes provide visual confirmation that a disc has been discharged from each of the dispensers. Weights and spring clips in the cartridges push the discs successively into firm contact with the dispensing slide plates for dependably delivering them into the dispenser chutes.

32 Claims, 15 Drawing Figures

Fig.1.

DISC DISPENSER WITH REMOVABLE MAGAZINES

BACKGROUND OF THE INVENTION

Mechanisms for dispensing antibiotic saturated discs from tubular cartridges are described in U.S. Pats. NO. 3,031,819, 3,032,179, 3,036,703 and 3,115,992 and Canadian Pat. No. 687,149.

Some of these dispensers simultaneously drop a number of discs into a culture dish or into separate compartments of solutions for comparing the effectiveness of the different antibiotics. Such multiple disc dispensers are subject to malfunctions which are significant because the failure to discharge even only one of the array of discs ruins the test. An object of this invention is, therefore, to provide a multiple disc dispenser which is dependable in operation and in which malfunctions may be readily detected and corrected.

SUMMARY

A number of individual self-contained antibiotic disc dispensers capable of dispensing single discs in response to an actuating movement are locked into apertured sockets on a base frame. A drive mechanism operates an actuating linkage, which simultaneously operates each of the individual dispensers to discharge discs through the base frame. An adjustable support, such as a cam profiled adjusting ring may support the base frame at an adjustable height above a culture medium into which it dispenses the discs. Yieldable detent and indexing projections indicate the height of the dispenser above the culture medium. The individual dispensers may each include a chute body, a springbiased shouldered slide carriage plate, a cover and a cartridge. The upper ends of the chutes are maintained open to permit the operator to visually verify that all discs are discharged. A manually actuated plunger may drive the actuating plate through a crank, and the actuating plate may engage actuating pins on each of the individual dispensers. The individual dispensers are locked in the sockets by an apertured locking plate which engages over lugs at the bottom ends of the chutes. The actuating and locking plates are apertured to permit the chutes and discs to pass through them. Smooth dependable feeding of the discs from the dispenser cartridges is facilitated by improved nonbinding weighted clips which push the discs down through the tubular cartridges.

BRIEF DESCRIPTION OF THE DRAWINGS

Novel features and advantages of the present invention will become apparent to one skilled in the art from a reading of the following description in conjunction with the accompanying drawings wherein similar reference characters refer to similar parts and in which.

DESCRIPTION OF THE EMBODIMENT

Figure 1:
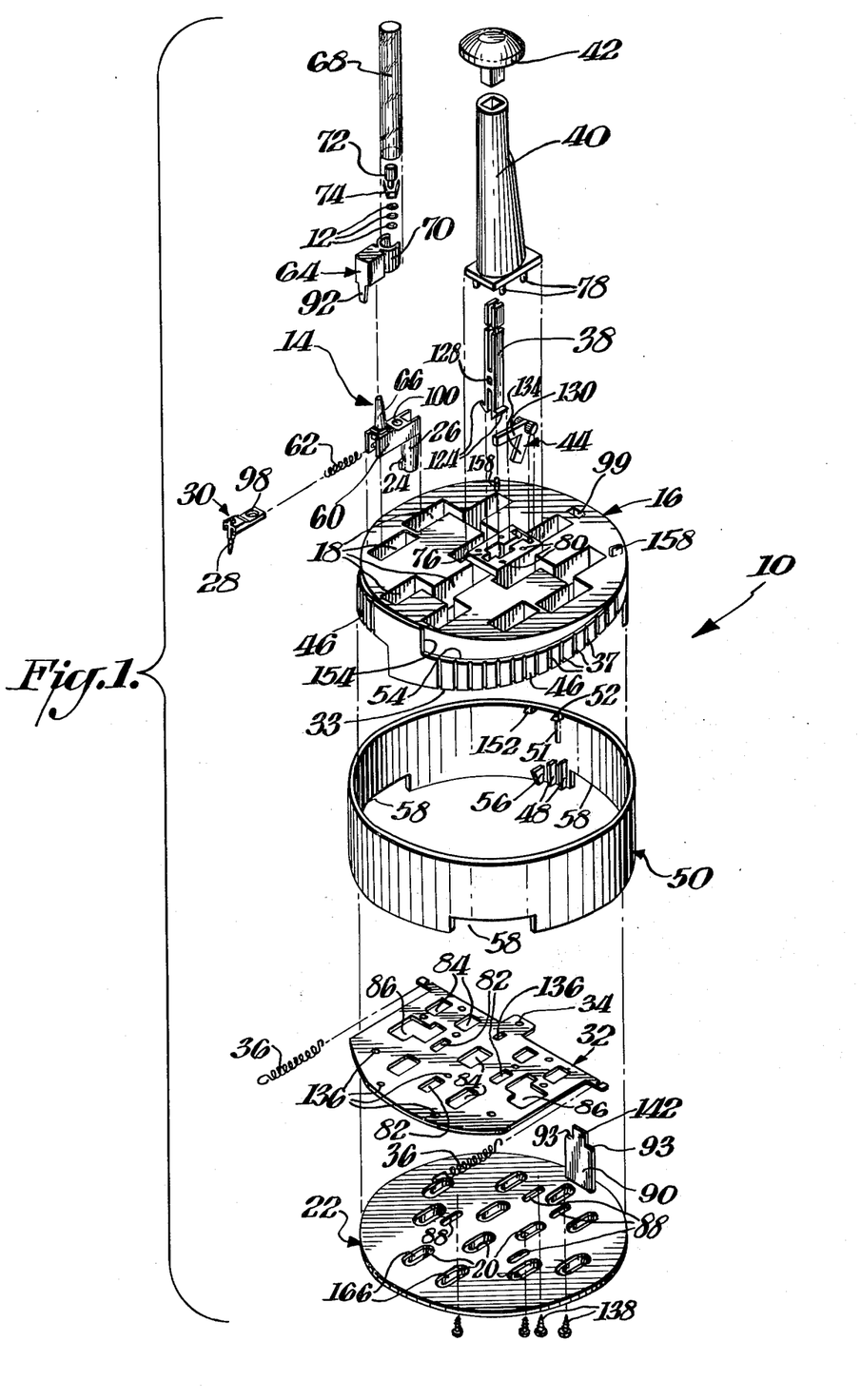
FIG. 1 is an exploded three-dimensional view of one embodiment of this invention.
Figures 2, 3, 4, 5:
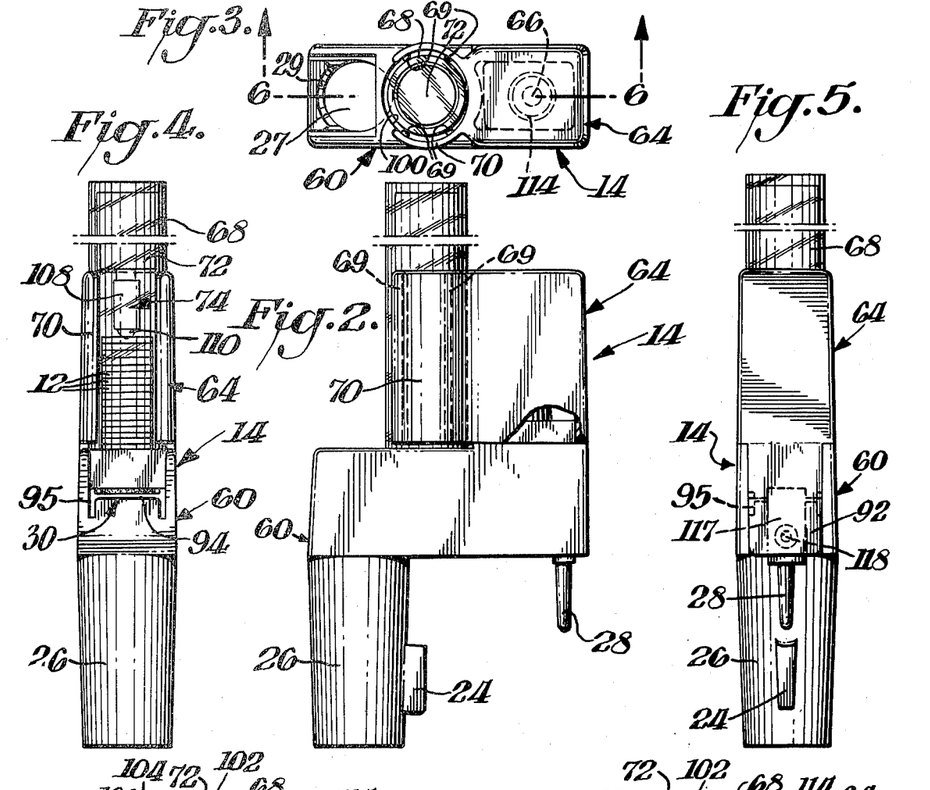
FIG. 2 is a side view in elevation of one of the individual dispensers incorporated in the embodiment shown in FIG. 1.
FIG. 3 is a top plan view of the individual dispenser shown in FIG. 2.
FIG. 4 is a left-end elevational view of the individual dispenser shown in FIG. 2.
FIG. 5 is a right-end elevational view of the individual dispenser shown in FIG. 2.

In FIG. 1 is shown an antibiotic disc dispenser 10 for simultaneously dispensing an array of antibiotic discs 12 from an array of twelve individual self-contained disc dispensers 14 mounted on base frame 16 in apertured sockets 18 and locked therein by engagement of a side of apertures 20 in locking plate 22 over lugs 24 at the lower ends of chutes 26 disposed below dispensers 14. Dispenser 14 is operated by pushing actuating plate 32 against pin 28 on slide carriage 30 through engagement of pin 28 within one of pin slots 34 in actuating plate 32. Actuating plate 32 is moved against the force of return springs 36 by plunger 38 mounted on top of dispenser 10 within guide tube 40. Plunger 38 is actuated by downward pressure on knob 42 and its motion is transmitted to actuating plate 32 by crank 44.

Base frame 16 is supported at an adjustable height above a culture dish (later shown) by sliding disposal of the bottom edges 33 of three profiled cam strips 46 upon three sets of two uneven follower ribs 48 within height-adjusting ring 50. Upper retaining projections 52 within height-adjusting ring 50 engage over the top edges 54 of profiled cam strips 46 and cooperate with the tops of follower ribs 48 in holding profiled cam strips 46 between them. Angular projections 56 within the bottom edge of ring 50 center a culture dish within the bottom of dispenser 10, and slots 58 prevent air locks from blocking operation of the dispenser. Detent rib 51 below retaining or holddown projections 52 yieldably engage slots 37 for indexing the relative angular portions of ring 50 about base frame 16 and the height adjustment obtained thereby.

Individual dispenser 14 shown in FIG. 1 includes chuted body 60 within which slide carriage 30 moves against the force of compression spring 62 and upon which cover 64 is mounted on horn 66. Cartridge tube 68 is inserted between internal contact ridges 69 in clamp 70 on the front of cover 64 and contains weight 72 pushing down on feed clip 74 which rests on the stack of antibiotic discs 12 to be discharged by dispenser 14 as later described.

Plunger guide tube 40 is secured on pedestal 76 on top of base frame 16 by insertion of four pins 78 in corresponding pin holes 80 on top of pedestal 76 and cementing thereto. Actuating plate 32 is secured to slide under base frame 16 by retaining screws (later shown) inserted through three slots 82. Apertures 84 and 86 permit chutes 26 of dispensers 14 to pass through them. Locking holes 20 in locking plate 22 also permit passage of chutes 26 and discs discharged through them and lock over lugs 24 on chutes 26. Locking plate 22 is mounted to slide back and forth under base frame 16 by screws (later shown) through four slots 88. Vertical tab 90 at the rear of locking plate 22 extends upwardly through base frame 16 as later described and permits mnovement of the locking plate from above dispenser 10.

Details of self-contained dispensers 14 are shown in FIGS. 2–7. Dispenser 14 is shown in an unactuated condition in FIGS. 2–6 with the return movement of slide carriage 30 arrested by tail plate 92 of cover 64. The apertured end 94 of slide plate 95 remote from pin 28 is thinner than the rear end 96 to dispose disc feeding aperture 98 in a thinner shouldered portion 94 of slide plate 95. This facilitates smooth operation of slide carriage 30 and dependable feeding of discs 12. The thicker rear portion 96 of slide plate 95 smoothly confines discs 12 within tubular cartridge 68, which is inserted within shouldered socketed funnel 100 in body 60.

Figure 6:
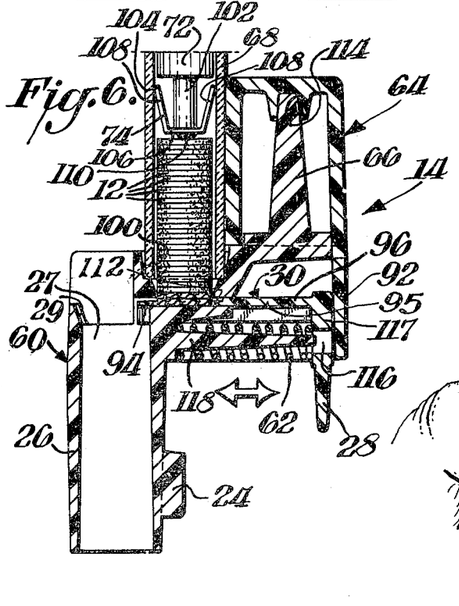
FIG. 6 is a cross-sectional view taken through FIG. 3 along the line 6—6 in the unactuated condition.

Weight 72 in tube 68 has a bottom stem 102 disposed against the bottom of angular U-shaped clip 74 to urge it downwardly. Weight 72 weighs, for example, 4 grams and clip 74, which is for example made of spring material such as beryllium copper, causes about two grams of frictional resistance in rubbing against the inner walls of tubes 68, to leave a resultant two grams of force pushing down on the stack of discs 12. Points 104 of clip 74 ratchet the downward movement of clip 74 and maintain the stack of discs 12 firmly packed together. The disposition of stem 102 of weight 72 on the bottom arm 106 of clip 74, clear of side arms 108, prevents weight 72 from bending clip 74 and interfering with the efficient operation of clip 74. Dimple 110 at the center of bottom end 106 of clip 74 is higher than slot 112 in body 60 through which slide 30 passes to prevent clip 74 from dropping into aperture 98 and binding operation of slide 30.

Figure 7:
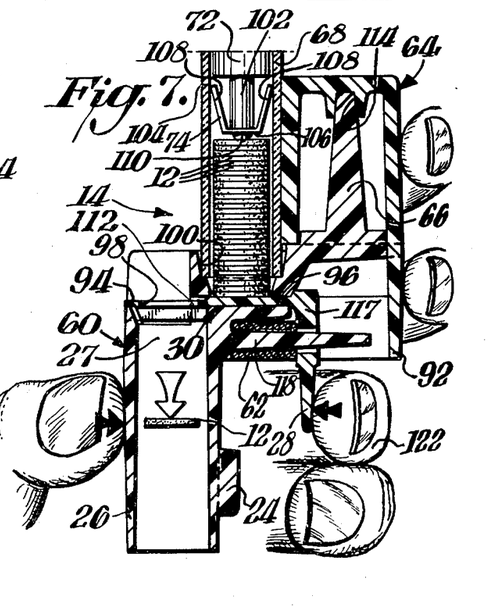
FIG. 7 is a cross-sectional view similar to FIG. 6 in the actuated condition.

FIGS. 6 and 7 show the engagement of socket 114 within cover 64 over horn 66 on body 60. Clearing hole 116 in the rear actuating end 117 of slide carriage 30 passes over tapered guide shaft 118 on body 60 about which compression spring 62 is mounted. The rearward movement of slide carriage 30 is arrested by tail plate 92 extending downwardly from cover 64. Forward movement of slide 30 from the position shown in FIG. 6 to that shown in FIG. 7 carries a disc 12 from the stack in cartridge 68 over the open upper end 27 of chute 26 through which it is dropped. Dispenser 14 is shown being manually actuated by fingers 122 in FIG. 7, which is the manner in which dispensers 14 are individually used. Dispensers 14 are also capable of simultaneous multiple operation when mounted on base frame 16 as otherwise described herein. Semicircular portion 29 of the upper rim of open end 27 of chute 26 is chamfered to help direct discharged discs 12 into chute 26.

Figures 8, 8A, 9, 10:
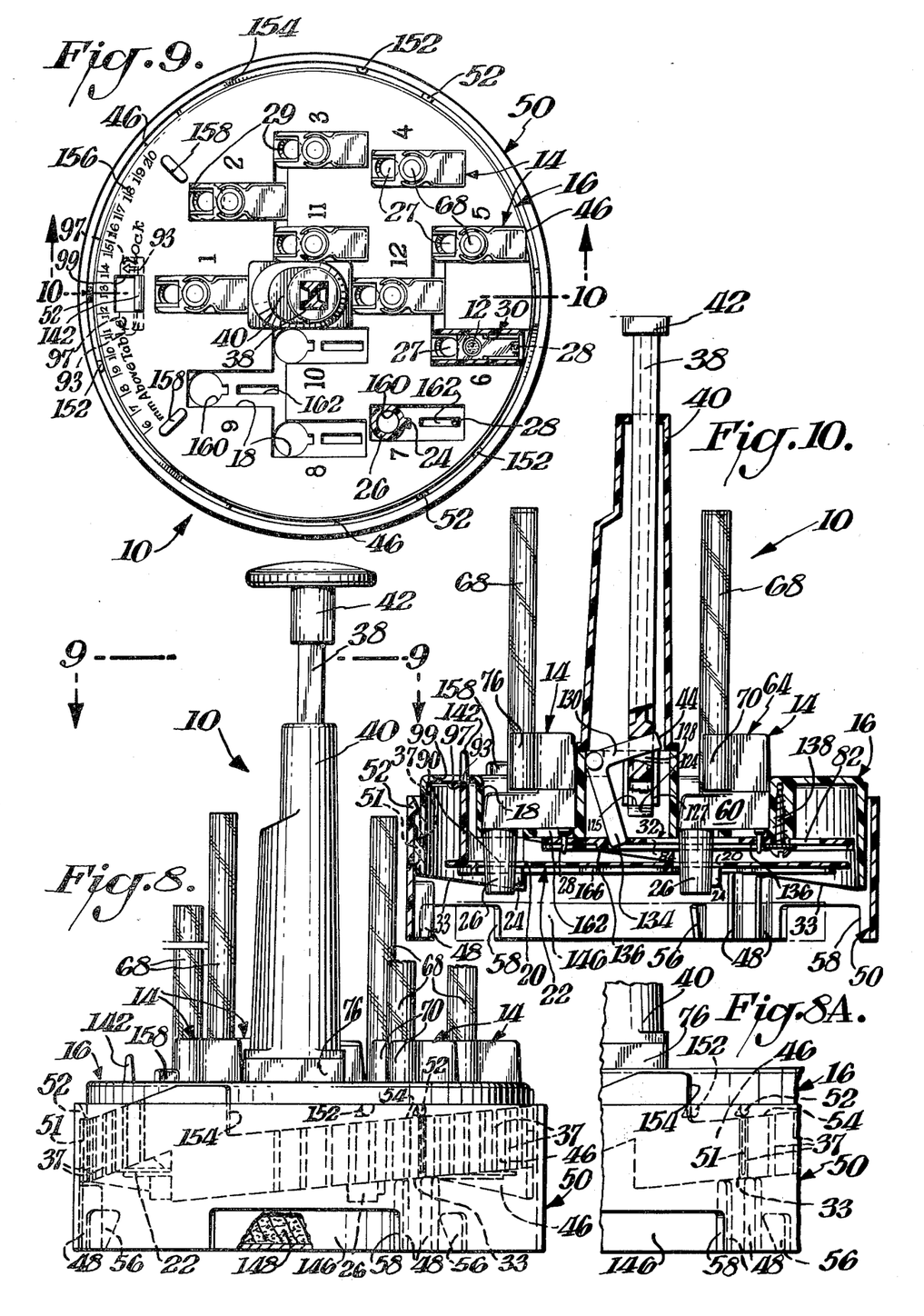
FIG. 8 is a side view in elevation of an assembled embodiment of this invention (of which an exploded view is shown in FIG. 1) in an intermediate position of height adjustment.
FIG. 8A is a fragmental view of a lower central portion of the embodiment shown in FIG. 8 in the upper position of height adjustment.
FIG. 9 is a cross-sectional view taken through FIG. 8 along the line 9—9.
FIG. 10 is a cross-sectional view taken through FIG. 9 along the line 10—10.
Figures 11, 12, 13, 14:
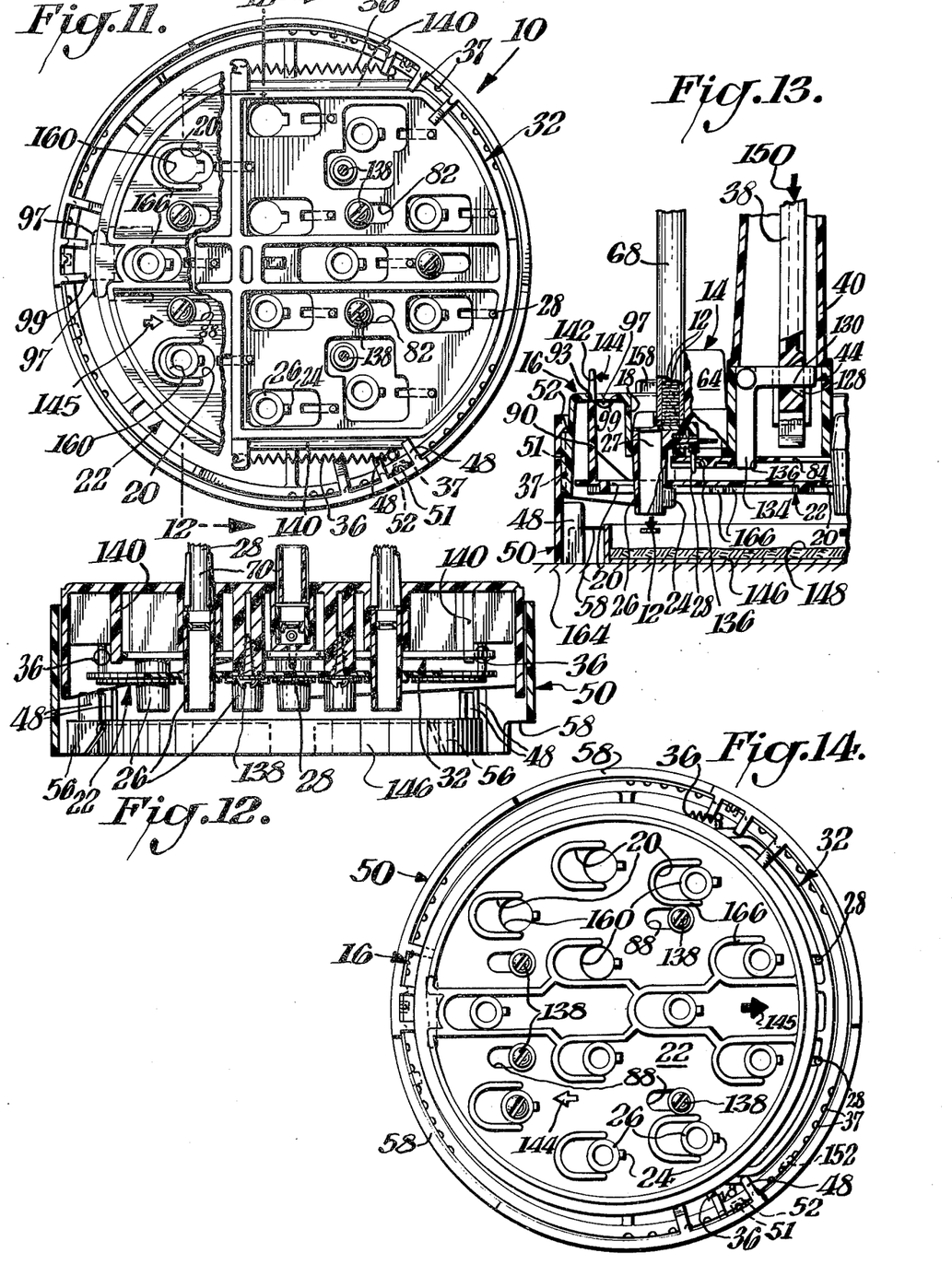
FIG. 11 is a bottom plan view of the embodiment shown in FIG. 8 with most of the locking plate removed.
FIG. 12 is a cross-sectional view taken through FIG. 11 along the line 12—12 in the unactuated condition.
FIG. 13 is a fragmental cross-sectional view taken through the lower lefthand portion of the embodiment shown in FIG. 8 in the actuated condition.
FIG. 14 is a bottom plan view of the embodiment shown in FIG. 8 in the locked condition.

FIGS. 9–14 show how dispensers 14 are mounted and locked on base frame 16 and actuated by operation of plunger 38 by pushing down on knob 42. Downward pressure on knob 42 moves the lower split prongs 124 of plunger 38 downwardly against the force of actuating plate return springs 36 and return springs 62 on individual dispensers 14. Arm 130 of crank 132 is inserted through hole 128 in plunger 38 and lower crank arm 134 is engaged in slot 136 in actuating plate 32 to urge it to the left as shown in FIGS. 10 and 11 against the force of return springs 36. Shoulders 125 on prongs 124 engage under the lower ends of plunger socket 127 to prevent plunger 38 from being lifted out of base frame 16.

Actuating plate 32 is maintained in sliding engagement below base frame 16 as shown in FIGS. 10–12 by insertion of three machine screws 138 through slots 82 and the disposition of the sides of actuating plate 32 between guide ridges 140 at the bottom of base frame 16. The reciprocating movement of actuating plate 32 is more than sufficient to move slide carriages 30 of dispensers 14 by engagement of actuating pins 28 in pin slots 34 in actuating plate 32, through a distance which moves apertures 98 and the discs carried in them over the opening 27 on top of chute 26 with sufficient overtravel to insure operation of each of dispensers 14, each time plunger 38 is moved downwardly through its full stroke.

Locking plate 22 is mounted within base frame 16 below actuating plate 32 as shown in FIGS. 10–14 and is locked by movement of vertical tab 90 by finger pressure on upper end 142 in the direction of arrow 144 as shown in FIG. 13. Upper end 142 of vertical tab 90 is of a reduced width dimension forming shoulders 93. Shoulders 93 engage cam surfaces 97 disposed to either side of slot 99 through which upper end extension 142 projects. Actuating plate 32 is maintained locked in its disengaged or engaged position by disposition of shoulders 93 on either side of cam surfaces 97 and contact of end extension 142 with rearward or forward edge of slot 99.

As shown in FIG. 12, chutes 26 of dispensers 14 pass through the previously described slots 84 and 86 in actuating plate 32 and slots 20 in locking plate 22 (which engage lugs 24 on chutes 26) to dispose them above culture dish 146 as shown in FIGS. 8, 8A, 12 and 13. FIG. 13 shows a disc 12 dropping from chute 26 onto agar medium 148 in dish 146. Twelve such discs are simultaneously dispensed from array of dispensers 14 on each downward movement of plunger 68, as shown in FIG. 13 in the direction of arrow 150.

The height of base frame 16 and dispensers 14 above a supporting surface for it and culture dish 146 and contained medium 148 is adjusted by the angular engagement of adjusting ring 50 with base frame 16. This adjustment is provided by the angular disposition of profiled cam strips 46 on inner follower support ribs 48 of slightly different height within support ring 50 as previously described in conjunction with FIG. 1. Profiled cam strips 46 are yieldably held between upper ends of support projections 48 and upper retaining projection 52. Since all of the parts of dispenser 10 with the exception of the metal springs and glass cartridge tubes are made of resilient plastic material, such as a polycarbonate, the engagement of profiled cam strips between projections 48 and 52 and other engaged portions of the apparatus, is readily disengageable.

Stop projections 152, also within the upper portion of adjusting ring 50 yieldably abut against the terminal ends 154 of profiled cam strips 46 to indicate the limit of raised movement of adjusting ring 50 relative to base frame 16 as shown in FIG. 8A. In this position, the height of the bottom of the chutes 26 above a surface supporting it and a culture dish 146, such as a Petri dish, is, for example, approximately 20 mm., which is the largest magnitude indicia 156 shown marked on the top edge of base frame 16 in FIG. 9. The lowest height marked on scale of indicia 156 is 6 mm., which is above the table upon which culture dish 146 and dispenser 10 are disposed. For a standard agar thickness of approximately 3 to 5 mm. in a dish having a bottom about 1 to 2 mm. thick, this provides a minimum clearance of about 3 mm. above the upper surface of the agar medium. The 14 mm. range of adjustment permits a variety of dishes and agar deposits to be accommodated under dispenser 10. Indexing of angular height-adjusting movement of ring 50 relative to base frame 16 is accomplished by the yieldable engagement of outer indexing ribs 51 on cam strips 46 within adjusting ring 50 below retaining projections 52.

FIG. 9 also shows a pair of tabs 158 adjacent the ends of height indicia 156, which provide a means for grasping base frame 16 and holding it steady while height adjusting ring 50 is rotated relative to it in changing the height of base frame 16 above a surface 164 (shown in FIG. 13). FIG. 9 also shows the upper end 142 of vertical tab 90 in the locked position with shoulders 93 inside of cam surfaces 97 at the inner end of slot 99. Apertured sockets 18 of rectangular outline have keyhole-shaped apertures in their bases which receive chutes 26, one of which is shown in a socket 18 at the lower right-hand portion of FIG. 9 with its locking lug 24. Sockets 18 also have elongated slots 162 in their bases which permit actuating pins 28 to extend through and below base frame 16. There are twelve apertured sockets shown in FIG. 9, which are accordingly numbered from 1 through 12. Some of them have complete dispensers 14 inserted within them and others only have partial dispensers 14 inserted within them to illustrate various features including the open tops 27 of chutes 26 which permit the discharge of discs 12 from all dispensers 14 to be visually verified. FIG. 9 also shows upper retaining projections 52 above profiled cam strips 46 and stop projections 152 which contact terminal ends 154 of profiled cam strips 46.

FIG. 14 shows the locked position of locking plate 22 in which locking apertures 20 are in the left-hand position, (in the direction of arrow 144) engaged about locking lugs 24 of dispensers chutes 26. When locking plate 22 is moved to the right in the direction of arrow 145, it assumes the unlocked position shown at the left-hand side of FIG. 11 in which apertures 20 are moved to their right-hand position clear of keyhole-shaped apertures 160 through which chutes 26 and locking lugs 24 are inserted or removed. FIGS. 11–14 also show U-shaped stiffening ribs 166 on the left-hand sides of locking apertures 20 and which therefore do not interfere with the locking function of apertures 20.

I claim:

1. A disc dispenser for simultaneously dispensing a number of discs comprising a base frame, a number of individual self-contained disc dispensers capable of dispensing single discs in response to an actuating movement, each of said individual dispensers having a body and a cartridge containing a plurality of discs connected to said body, a tubular chute disposed on each body extending in an opposite direction from said cartridge, apertured sockets in said base frame for receiving said bodies of said individual disc dispensers with said tubular chutes extending through the apertures whereby said disc dispensers are mounted upon said base frame in position for simultaneously dispensing their discs through apertures in said base frame with said cartridges disposed above said base frame whereby they are visually and physically accessible while said bodies are disposed within said sockets, a detachable connecting means on each of said bodies for removably connecting a cartridge to each of said bodies whereby each of said cartridges may be removed and be connected to said body while each of said dispensers is mounted on said base frame, a locking means on said disc dispenser and said base frame for securing said disc dispensers to said base frame, an actuating element on each of said bodies of said disc dispensers, an actuating linkage mounted on said base frame, said actuating linkage engaging said elements, and a drive mechanism mounted on said base frame connected with said actuating linkage whereby said actuating linkage is moved for simultaneously operating said elements and simultaneously dispensing discs from each of the said individual dispensers.

2. A disc dispenser as set forth in claim 1 wherein an adjustable support means is engaged with said base frame and extending below it for supporting said base frame at an adjustable height above a base surface.

3. A disc dispenser as set forth in claim 2 wherein said adjustable support means comprises an adjustable support ring.

4. A disc dispenser as set forth in claim 3 wherein cam and follower means adjustably connects said support ring to said base frame.

5. A disc dispenser as set forth in claim 4 wherein said base frame and support ring are cylindrical.

6. A disc dispenser as set forth in claim 5 wherein said support ring is larger in diameter than said base frame, and said base frame is movably engaged within said support ring.

7. A disc dispenser for simultaneously dispensing a number of discs comprising a base frame, a number of individual self-contained disc dispensers capable of dispensing single discs in response to an actuating movement, each of said individual dispensers having a body and a cartridge containing a plurality of discs connected to said body, apertured sockets in said base frame for receiving said bodies of said individual disc dispensers whereby said disc dispensers are mounted upon said base frame in position for simultaneously dispensing their discs through apertures in said base frame, a locking means on said disc dispenser and said base frame for securing said disc dispensers to said base frame, an actuating element on each of said bodies of said disc dispensers, an actuating linkage mounted on said base frame, said actuating linkage engaging said elements, a drive mechanism mounted on said base frame connected with said actuating linkage whereby said actuating linkage is moved for simultaneously operating said elements and simultaneously dispensing discs from each of the said individual dispensers, an adjustable support means is engaged with said base frame and extending below it for supporting said base frame at an adjustable height above a base surface, said adjustable support means comprises an adjustable support ring, cam and follower means adjustably connects said support ring to said base frame, said base frame and support ring are cylindrical, said support ring is larger in diameter than said base frame, said base frame is movably engaged within said support ring, said cam and follower means comprises profiled cam strips on the outer periphery of said base frame, and supporting follower ribs within said support ring upon which said profiled cam strips rest for supporting said base frame at an adjustable height above said base surface.

8. A disc dispenser as set forth in claim 7 wherein a series of indexing slots is disposed upon the outer periphery of said base frame, and a detent rib is mounted within the periphery of said adjusting ring for yieldably engaging said indexing slots and indexing relative angular movement of said adjusting ring about said base frame and the height of said base frame above said base surface.

9. A disc dispenser as set forth in claim 8 wherein said cam profiled strips comprise three cam strips disposed about the periphery of said base frame in a sawtoothed manner having substantially vertical terminal ends disposed between them.

10. A disc dispenser as set forth in claim 9 wherein stop lugs are disposed within the periphery of said adjusting ring for engaging said terminal ends of the cam surfaces to indicate the upper and lower extremities of height adjustment of said base frame.

11. A disc dispenser as set forth in claim 10 wherein said lug is yieldable to permit the terminal ends to be passed.

12. A disc dispenser as set forth in claim 7 wherein said supporting follower ribs comprise at least a pair of ribs of slightly uneven height.

13. A disc dispenser as set forth in claim 12 wherein a retaining projection is disposed within an upper portion of said adjusting ring a distance away from the tops of said support ribs which is substantially equal to the height of said profiled cam strips whereby said cam strips are disengageably retained within said support ribs and said retaining projection.

14. A disc dispenser as set forth in claim 12 wherein apertures are provided in said adjusting ring to prevent air locks from interfering with the operation of said dispenser.

15. A disc dispenser as set forth in claim 14 wherein said drive mechanism comprises a reciprocating plunger device mounted upon said base frame, and a crank connects said reciprocating plunger device to said actuating plate.

16. A disc dispenser for simultaneously dispensing a number of discs comprising a base frame, a number of individual self-contained disc dispensers capable of dispensing single discs in response to an actuating movement, each of said individual dispensers having a body and a cartridge containing a plurality of discs connected to said body, apertured sockets in said base frame for receiving said bodies of said individual disc dispensers whereby said disc dispensers are mounted upon said base frame in position for simultaneously dispensing their discs through apertures in said base frame, a locking means on said disc dispenser and said base frame for securing said disc dispensers to said base frame, an actuating element on each of said bodies of said disc dispensers, an actuating linkage mounted on said base frame, said actuating linkage engaging said elements, a drive mechanism mounted on said base frame connected with said actuating linkage whereby said actuating linkage is moved for simultaneously operating said elements and simultaneously dispensing discs from each of the said individual dispensers, said actuating element on each of said disc dispensers comprises an actuating pin, and pin holes in said actuating plate within which said actuating pins are inserted whereby sliding movement of said actuating plate simultaneously operates each of said dispensers.

17. A disc dispenser as set forth in claim 16 wherein said reciprocating plunger device comprises a guide tube substantially vertically mounted on said base frame and a plunger rod mounted to slide up and down within said guide tube.

18. A disc dispenser for simultaneously dispensing a number of disc comprising a base frame, a number of invidual self-contained disc dispensers capable of dispensing single disc in response to an actuating movement, each of said individual dispensers having a body and a cartridge containing a plurality of discs connected to said body, apertured sockets in said base frame for receiving said bodies of said individual disc dispensers whereby said disc dispensers are mounted upon said base frame in position for simultaneously dispensing their discs through apertures in said base frame, a locking means on said disc dispenser and said base frame for securing said disc dispensers to said base frame, an actuating element on each of said bodies of said disc dispensers, an actuating linkage mounted on said base frame, said actuating linkage engaging said elements, a drive mechanism mounted on said base frame connected with said actuating linkage whereby said actuating linkage is moved for simultaneously operating said elements and simultaneously dispensing discs from each of the said individual dispensers. said locking means comprises an apertured locking plate disposed below said base frame, slide means connectng said locking plate to slide back and forth under said base frame, dispensing chutes on the bottoms of each of said individual disc dispensers, locking lugs on lower portions of said chutes and apertures in said apertured locking plate for receiving said chutes, and said locking plates having a range of sliding movement which optionally releases and engages said lugs for optionally securing said individual dispensers to said base frame with said chutes extending through said locking plate.

19. A disc dispenser for simultaneously dispensing a number of dics comprising a base frame, a number of individual self-contained disc dispensers capable of dispensing single discs in response to an actuating movement, each of said individual dispensers having a body and a cartridge containing a plurality of discs connected to said body, apertured sockets in said base frame for receiving said bodies of said individual disc dispensers whereby said disc dispensers are mounted upon said base frame in position for simultaneously dispensing their discs through apertures in said base frame, a locking means on said disc dispenser and said base frame for securing said disc dispensers to said base frame, an actuating element on each of said bodies of said disc dispensers, an actuatng linkage mounted on said base frame, said actuating linkage engaging said elements, a drive mechanism mounted on said base frame connected with said actuating linkage whereby said actuating linkage is moved for simultaneously operating said elements and simultaneously dispensing discs from each of the said individual dispensers, a discharge chute for each of said individual dispensers is provided in line with the apertures in said sockets, and said chutes having open upper ends to permit the discharge of discs through all of said chutes to be verified.

20. An individual disc dispenser comprising a small elongated body whereby said dispenser is held for dispensing manually or mechanically, a slot extending through said body, a socketed funnel in said body intersecting said slot, a tubular chute in said body intersecting said slot adjacent and spaced from said socketed funnel, a slide carriage having a slide plate disposed in said slot for sliding movement therein, the chute end of said plate having an aperture for receiving said discs, said chute end of said slide plate being thinner than the funnel end thereby providing a thin shouldered end on said plate containing said aperture whereby discharge of said discs from said funnel into said aperture is facilitated, a cover being mounted upon and above said body on a side opposite from said tubular chute, said cover having a retainer disposed above said socketed funnel for securing said cartridge above and within said socketed funnel, resilient means urging said slide carriage to the loaded position in which said aperture is disposed below said socket, and an actuating pin on said slide carriage disposed opposite from said chute with said socketed funnel disposed inbetween them whereby actuating movement is imparted to it for moving a disc loaded in said aperture over and into said chute.

21. A disc dispenser as set forth in claim 20 for dispensing discs from a tubular cartridge wherein a cover is mounted upon said body, said cover having a retainer disposed above said socketed funnel for securing said cartridge above and within said socketed funnel, and said cover having a tail plate for restraining the movement of said slide carriage away from said chute and said socketed funnel.

22. A disc dispenser comprising a body, a slot extending through said body, a socketed funnel in said body intersecting said slot, a tubular chute in said body intersecting said slot adjacent and spaced from said socketed funnel, a slide carriage having a slide plate disposed in said slot for sliding movement therein, the chute end of said plate having an aperture for receiving said discs, said chute end of said slide plate being thinner than the funnel end thereby providing a thin shouldered end on said plate containing said aperture whereby discharge of said discs from said funnel into said aperture is facilitated, resilient means urging said slide carriage to the loaded position in which said aperture is disposed below said socket, an actuating pin on said slide carriage whereby actuating movement is imparted to it for moving a disc loaded in said aperture over and into said chute, a cover is mounted upon said body, said cover having a retainer disposed above said socketed funnel for securing said cartridge above and within said socketed funnel, said cover having a tail plate for restraining the movement of said slide carriage away from said chute and said socketed funnel, and said retainer on said cover comprises a pair of clamping fingers.

23. A disc dispenser comprising a body, a slot extending through said body, a socketed funnel in said body intersecting said slot, a tubular chute in said body intersecting said slot adjacent and spaced from said socketed funnel, a slide carriage having a slide plate disposed in said slot for sliding movement therein, the chute end of said plate having an aperture for receiving said discs, said chute end of said slide plate being thinner than the funnel end thereby providing a thin shouldered end on said plate containing said aperture whereby discharge of said discs from said funnel into said aperture is facilitated, resilient means urging said slide carriage to the loaded position in which said aperture is disposed below said socket, and an actuating pin on said slide carriage whereby actuating movement is imparted to it for moving a disc loaded in said aperture over and into said chute, a cover is mounted upon said body, said cover having a retainer disposed above said socketed funnel for securing said cartridge above and within said socketed funnel, said cover having a tail plate for restraining the movement of said slide carriage away from said chute and said socketed funnel, said slide carriage comprises a slide plate and a rear actuating end, a guide shaft on said body, an aperture in said rear actuating end of said slide carriage for engaging over said guide shaft, and a compression spring disposed over said guide shaft and reacting between said body and said rear end of said slide carriage for returning it to the loaded position against said tail plate of said cover.

24. A disc dispenser as set forth in claim 23 wherein a horn extends upwardly from said body substantially parallel to said socketed funnel, and said cover includes a socket in its upper end which engages the top of said horn for mounting said cover on said body.

25. A disc dispenser comprising a body, a slot extending through said body, a socketed funnel in said body intersecting said slot, a tubular chute in said body intersecting said slot adjacent and spaced from said socketed funnel, a slide carriage having a slide plate disposed in said slot for sliding movement therein, the chute end of said plate having an aperture for receiving said discs, said chute end of said slide plate being thinner than the funnel end thereby providing a thin shouldered end on said plate containing said aperture whereby discharge of said discs from said funnel into said aperture is facilitated, resilient means urging said slide carriage to the loaded position in which said aperture is disposed below said socket, an actuating pin on said slide carriage whereby actuating movement is imparted to it for moving a disc loaded in said aperture over and into said chute, and said top of said tubular chute is open to permit the discharge of discs through said chute to be visually verified.

26. A disc dispenser comprising a body, a slot extending through said body, a socketed funnel in said body intersecting said slot, a tubular chute in said body intersecting said slot adjacent and spaced from said socketed funnel, a slide carriage having a slide plate disposed in said slot for sliding movement therein, the chute end of said plate having an aperture for receiving said discs, said chute end of said slide plate being thinner than the funnel end thereby providing a thin shouldered end on said plate containing said aperture whereby discharge of said discs from said funnel into said aperture is facilitated, resilient means urging said slide carriage to the loaded position in which said aperture is disposed below said socket, an actuating pin on said slide carriage whereby actuating movement is imparted to it for moving a disc loaded in said aperture over and into said chute, and in combination with a base frame wherein a locking lug is disposed on a lower portion of said chute for optionally securing said dispenser to said base frame.

27. A disc dispenser comprising a body, a slot extending through said body, a socketed funnel in said body intersecting said slot, a tubular chute in said body intersecting said slot adjacent and spaced from said socketed funnel, a slide carriage having a slide plate disposed in said slot for sliding movement therein, the chute end of said plate having an aperture for receiving said discs, said chute end of said slide plate being thinner than the funnel end thereby providing a thin shouldered end on said plate containing said aperture whereby discharge of said discs from said funnel into said aperture is facilitated, resilient means urging said slide carriage to the loaded position in which said aperture is disposed below said socket, an actuating pin on said slide carriage whereby actuating movement is imparted to it for moving a disc loaded in said aperture over and into said chute, in combination with a tubular disc-containing cartridge having a lower end disposed in said socketed funnel, a weighted feeding clip assembly in said cartridge above said discs for smoothly feeding them downwardly, said weighted clip assembly comprising a U-shaped clip having outwardly sloping arms with pointed ends for resiliently engaging the walls of said cartridge to ratchet the downward movement of said clip assembly, said weight having an upper larger diameter for smoothly sliding downwardly within said tubular cartridge, and said weight having a smaller lower tip end for bearing against the bottom of said U-shaped clip and urging it downwardly clear of pressure of said arms.

28. A disc dispenser as set forth in claim 27 wherein said clip has a projection on its lower end having a height greater than the thickness of said slot whereby said clip is prevented from entering within said aperture and blocking operation of said slide carriage.

29. A disc dispenser as set forth in claim 28 wherein said projection comprises a dimple.

30. A weighted feeding clip assembly for a tubular cartridge which feeds discs into a slot comprising a U-shaped clip having outwardly sloping arms with pointed ends for resiliently engaging the walls of said cartridge to ratchet the downward movement of said clip assembly, said clip having a bottom disposed between said outwardly sloping arms, a weight disposed against said bottom and between said outwardly sloping arms, said weight having an upper larger diameter for smoothly sliding downwardly within said tubular cartridge, and said weight having a smaller diameter lower stem for bearing against the bottom of said U-shaped clip and urging it downwardly clear of pressure on said arms.

31. A disc dispenser as set forth in claim 30 wherein said clip has a projection on its lower end having a height greater than the thickness of said slot whereby the lower end of said clip is held clear of said slot, and said projection having an inclined base whereby said projection and clip are cammed upwardly in response to a lateral movement against it whereby said lower end of said clip is prevented from jamming.

32. A disc dispenser as set forth in claim 31 wherein said projection comprises a dimple.

* * * * *